(12) United States Patent
Kawada et al.

(10) Patent No.: US 12,378,398 B2
(45) Date of Patent: Aug. 5, 2025

(54) BINDER

(71) Applicant: JAPAN VAM & POVAL CO., LTD., Osaka (JP)

(72) Inventors: Shotaro Kawada, Osaka (JP); Masatoshi Kawanishi, Osaka (JP)

(73) Assignee: JAPAN VAM & POVAL CO., LTD., Osaka (JP)

( * ) Notice: Subject to any disclaimer, the term of this patent is extended or adjusted under 35 U.S.C. 154(b) by 1115 days.

(21) Appl. No.: 17/291,839

(22) PCT Filed: Nov. 13, 2019

(86) PCT No.: PCT/JP2019/044506
§ 371 (c)(1),
(2) Date: May 6, 2021

(87) PCT Pub. No.: WO2020/100933
PCT Pub. Date: May 22, 2020

(65) Prior Publication Data
US 2021/0395507 A1    Dec. 23, 2021

(30) Foreign Application Priority Data
Nov. 13, 2018  (JP) ................ 2018-213351

(51) Int. Cl.
C08L 29/04   (2006.01)
A61K 9/16    (2006.01)
A61K 9/28    (2006.01)

(52) U.S. Cl.
CPC ............ *C08L 29/04* (2013.01); *A61K 9/1635* (2013.01); *A61K 9/1682* (2013.01); *A61K 9/284* (2013.01)

(58) Field of Classification Search
CPC . C08L 29/04; C08L 2205/025; A61K 9/1635; A61K 9/1682; A61K 9/284; A61K 9/2027; A61K 31/167; C08J 2329/04; C08J 3/12; C08K 5/053; C08K 5/20; C08K 9/08; C08F 8/12
See application file for complete search history.

(56) References Cited

U.S. PATENT DOCUMENTS

| | | | |
|---|---|---|---|
| 5,532,274 A * | 7/1996 | Wenzel ................ | A61K 31/195 514/567 |
| 5,624,960 A | 4/1997 | Wenzel et al. | |
| 2006/0229383 A1 | 10/2006 | Noami et al. | |
| 2012/0329936 A1 | 12/2012 | Noami et al. | |

(Continued)

FOREIGN PATENT DOCUMENTS

| CN | 106715492 | 5/2017 |
|---|---|---|
| EP | 1 657 265 | 5/2006 |

(Continued)

OTHER PUBLICATIONS

Makoto et al. (JP2017141299A Machine English Translation) (Year: 2017).*
"Pharmacology", compiled by Nanjing Pharmacy College, Beijing: People's Medical Publishing House (published on Mar. 31, 1978), p. 425, with English translation.

(Continued)

*Primary Examiner* — Robert A Wax
*Assistant Examiner* — Quanglong N Truong
(74) *Attorney, Agent, or Firm* — Wenderoth, Lind & Ponack, L.L.P.

(57) ABSTRACT

A novel binder is provided. The binder comprises a polyvinyl alcohol-based polymer which has an average saponification value of 85.0 mol % to 89.0 mol % as measured according to JIS K6726 and meets requirement (A): based on data obtained by measurement of the polyvinyl alcohol-based polymer by liquid chromatography, a value represented by formula (3) shown below is 22 or more,
wherein the measurement is performed with a liquid chromatography system equipped with a charged aerosol detector and a Thermo Scientific Acclaim™ 300 column (catalog number: 060266, carbon load: 8%, maximum pressure: 4500 psi, particle size: 3 μm, pore size: 300 Å, stationary phase: C18, surface area: 100 m²/g, length: 150 mm, diameter: 4.6 mm, pH: 2.5 to 7.5, material: glass lined tubing) under the measurement conditions described below,
wherein the data represent a baseline-normalized intensity over a retention time of 5.0 to 12.0 minutes at a sampling interval of 500 ms, and
wherein the value represented by formula (3) is calculated from formulae (1) and (2) shown below, wherein the intensity at a retention time $T_i$ [min] is represented by $P_i$ [pA].

Measurement Conditions
Concentration of an aqueous polyvinyl alcohol-based polymer solution: 0.1% by mass
Injection volume of the aqueous polyvinyl alcohol-based polymer solution: 2 μL
Column temperature: 50° C.
Flow rate: 1.0 mL/min
Eluent: a mixed solvent of water and methanol
Eluent gradient conditions: the ratio of water and methanol in the eluent changes from 95:5 to 15:85 at a constant rate over a run time from minutes 0 to 10; and the ratio of water and methanol in the eluent is constant at 15:85 over a run time from minutes 10 to 15.

Formulae $T_n = \Sigma(T_i \times P_i)/\Sigma(P_i)$              Formula (1)

$T_w = \Sigma(T_i^2 \times P_i)/\Sigma(T_i \times P_i)$   Formula (2)

$\{(T_w/T_n)-1\} \times 1000$                Formula (3)

16 Claims, 1 Drawing Sheet

(56) References Cited

U.S. PATENT DOCUMENTS

| | | |
|---|---|---|
| 2017/0209377 A1 | 7/2017 | Furo et al. |
| 2017/0348242 A1 | 12/2017 | Kawada et al. |
| 2019/0216826 A1 | 7/2019 | Matono et al. |
| 2020/0170955 A1 | 6/2020 | Furo et al. |

FOREIGN PATENT DOCUMENTS

| | | |
|---|---|---|
| EP | 3 173 101 | 5/2017 |
| EP | 3 666 261 | 6/2020 |
| JP | 6-504543 | 5/1994 |
| JP | 2016-104729 | 6/2016 |
| JP | 2017-141299 | 8/2017 |
| WO | 2016/072179 | 5/2016 |
| WO | 2017/170858 | 10/2017 |

OTHER PUBLICATIONS

Extended European Search Report issued Jul. 27, 2022 in corresponding European Patent Application No. 19885169.3, 8 pages.

Liu Bulin et al."Pesticide Formulation Processing Technology 2nd Edition", Chemical Industry Press, p. 243, Oct. 31, 1988, with partial English translation.

"Analysis and Application of Hot Patent Technologies No. 3", Editor-in-Chief of Jiangsu Center for Patent Examination Collaboration of the Patent Office of the State Intellectual Property Office, Beijing Intellectual Property Press, p. 69, Sep. 30, 2017, with partial English translation.

International Preliminary Report on Patentability and Written Opinion of the International Searching Authority issued May 18, 2021 in International (PCT) Application No. PCT/JP2019/044506.

International Search Report (ISR) issued Jan. 28, 2020 in International (PCT) Application No. PCT/JP2019/044506.

\* cited by examiner

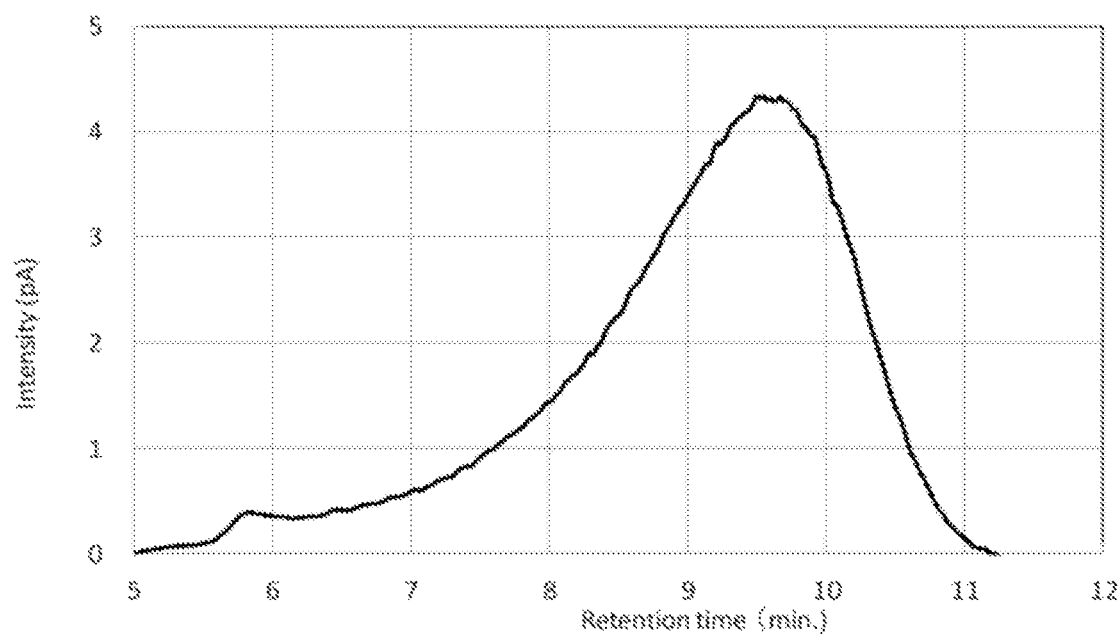

BINDER

TECHNICAL FIELD

The present invention relates to a binder etc.

BACKGROUND ART

Dosage forms of pharmaceutical products and health foods for oral ingestion of active ingredients are granules, tablets, powders, capsules, etc. For these applications, powder materials including medicinal substances and active ingredients are used, but in most cases, medicinal substances and active ingredients have a small particle diameter, drifting and dusting problems, and poor flowability and handleability.

For these reasons, such medicinal substances and active ingredients are usually subjected to granulation. Particularly, granulation in manufacturing pharmaceutical products etc. is also intended for improvement in tableting property, content uniformity, dissolution etc.

Patent Literature 1 (WO 2016/72179) discloses a composition comprising a specific polyvinyl alcohol-based polymer (hereinafter referred to as a PVA-based polymer) for film coating of solid preparations such as tablets.

CITATION LIST

Patent Literature

Patent Literature 1: WO 2016/72179

SUMMARY OF INVENTION

Technical Problem

An object of the present invention is to provide a novel binder and the like.

Solution to Problem

As described in Patent Literature 1, coating techniques (film coating) for tablets etc. using PVA-based polymers are known. Such coating is intended for masking, oxygen insulation, moisture-proofing, product appearance improvement, etc. and is totally different in purpose and application from binders.

For example, for binders used for production of granulated materials from powder particles, binding strength and viscosity should be enough to efficiently bind powder particles together. In contrast, for film coating of tablets, it is necessary to avoid adhesion between tablets as much as possible from the viewpoint of productivity etc., and viscosity and tackiness are to be improved rather than desired. In fact, Patent Literature 1 states that the use of a specific PVA-based polymer can solve the problem of tackiness and achieves less adhesion between tablets.

Under such circumstances, the present inventors eagerly sought to use PVA-based polymers as binders. As a result, the present inventors found that a specific PVA-based polymer is useful as a binder based on an idea that is totally different from that of Patent Literature 1 etc., which is intended for film coating. The present inventors further conducted a great deal of examination and then completed the present invention.

That is, the present invention relates to the following.

[1] A binder comprising a polyvinyl alcohol-based polymer, wherein the polyvinyl alcohol-based polymer has an average saponification value of 85.0 mol % to 89.0 mol % as measured according to JIS K6726 and meets requirement (A): based on data obtained by measurement of the polyvinyl alcohol-based polymer by liquid chromatography, a value represented by formula (3) shown below is 22 or more,
  wherein the measurement is performed with a liquid chromatography system equipped with a charged aerosol detector and a Thermo Scientific Acclaim™ 300 column (catalog number: 060266, carbon load: 8%, maximum pressure: 4500 psi, particle size: 3 μm, pore size: 300 Å, stationary phase: C18, surface area: 100 m²/g, length: 150 mm, diameter: 4.6 mm, pH: 2.5 to 7.5, material: glass lined tubing) under the measurement conditions described below,
  wherein the data represent a baseline-normalized intensity over a retention time of 5.0 to 12.0 minutes at a sampling interval of 500 ms, and
  wherein the value represented by formula (3) is calculated from formulae (1) and (2) shown below, wherein the intensity at a retention time $T_i$ [min] is represented by $P_i$ [pA].

Measurement Conditions
  Concentration of an aqueous polyvinyl alcohol-based polymer solution: 0.1% by mass
  Injection volume of the aqueous polyvinyl alcohol-based polymer solution: 2 μL
  Column temperature: 50° C.
  Flow rate: 1.0 mL/min
  Eluent: a mixed solvent of water and methanol
  Eluent gradient conditions: the ratio of water and methanol in the eluent changes from 95:5 to 15:85 at a constant rate over a run time from minutes 0 to 10; and the ratio of water and methanol in the eluent is constant at 15:85 over a run time from minutes 10 to 15.

Formulae $$T_n = \Sigma(T_i \times P_i)/\Sigma(P_i) \quad \text{Formula (1)}$$

$$T_w = \Sigma(T_i^2 \times P_i)/\Sigma(T_i \times P_i) \quad \text{Formula (2)}$$

$$\{(T_w/T_n)-1\} \times 1000 \quad \text{Formula (3)}$$

[2] The binder according to the above [1], wherein the value represented by formula (3) specified in requirement (A) is 30 or more.

[3] The binder according to the above [1] or [2], wherein the value represented by formula (3) specified in requirement (A) is 33 or more.

[4] The binder according to any one of the above [1] to [3], wherein a 4% by mass aqueous solution of the polyvinyl alcohol-based polymer has a viscosity of 2.0 to 10.0 mPa·s as measured according to JIS K6726.

[5] The binder according to any one of the above [1] to [4], wherein the binder is used for granulation.

[6] The binder according to any one of the above [1] to [5], wherein the binder is used for granulation from powder particles having an average particle diameter of 100 μm or less.

[7] The binder according to any one of the above [1] to [6], wherein the binder is used for production of a granulated material having an average particle diameter of 300 μm or less.

[8] A method for producing a granulated material by granulation (for example, wet granulation) using the binder (or the polyvinyl alcohol-based polymer) according to any one of the above [1] to [7].
[9] The method according to the above [8], wherein the method comprises a step of bringing an aqueous and/or water-based solution containing the binder (or the polyvinyl alcohol-based polymer) into contact with powder particles.
[10] A granulated material comprising the binder (or the polyvinyl alcohol-based polymer) according to any one of the above [1] to [7] as a binder (a granulated material comprising the binder according to any one of the above [1] to [7]).
[11] The granulated material according to the above [10], wherein the binder (or the polyvinyl alcohol-based polymer) is present in an amount of 0.005 to 0.1 part by mass relative to 1 part by mass of powder particles.
[12] A tablet comprising the granulated material according to the above [10] or [11].
[13] A coated tablet comprising the tablet according to the above [12] and a polyvinyl alcohol-based polymer coating a surface of the tablet.

Advantageous Effects of Invention

In one aspect of the present invention, a novel binder is provided. This binder comprises a PVA-based polymer but can function effectively as a binder.

In one aspect of the present invention, a binder that is useful for production of advantageous tablets is provided. For example, in the case where a granulated material (granules etc.) formed using the binder (the PVA-based polymer) of the present invention is used as a component of solid preparations (tablets etc.), advantageous solid preparations can be efficiently provided in terms of hardness and disintegrability (dissolution, moldability).

Originally, hardness and disintegrability (water disintegrability) are incompatible and have a trade-off relationship, but the binder of one aspect of the present invention can provide a good balance between hardness and disintegrability.

In one aspect of the present invention, a binder that is safe for oral and other applications is provided. The binder of the present invention comprises a PVA-based polymer having an average saponification value of 85.0 mol % to 89.0 mol %. This saponification value range of the PVA-based polymer, from 85.0 mol % to 89.0 mol %, is the same as that of commercially available PVAs for pharmaceutical use or pharmaceutical grade. This range also corresponds to the standard of the saponification value of PVA described in the official compendiums in Japan, the United States, and Europe.

BRIEF DESCRIPTION OF DRAWINGS

FIG. 1 is a chart plotting the intensity over a retention time of 5.0 to 12.0 minutes from the data obtained by the liquid chromatography measurement of a PVA-based polymer having an average saponification value of 88.2 mol % and a 4% by mass aqueous solution viscosity of 5.3 mPa·s.

DESCRIPTION OF EMBODIMENTS

Polyvinyl Alcohol-Based Polymer

The binder of the present invention comprises a polyvinyl alcohol-based polymer.

The polyvinyl alcohol-based polymer (may be referred to as a PVA-based polymer, PVA, etc.) (a) may usually be a saponified product of a vinyl ester-based polymer (a polymer at least composed of a vinyl ester as a polymerizable component).

The saponification value of the PVA-based polymer is not particularly limited and is preferably within the standard of the saponification value of PVA described in the following three official compendiums: the Japan Pharmaceutical Excipient Standards, the United States Pharmacopeia, and the European Pharmacopoeia. In addition, the average saponification value of the PVA-based polymer is, for example, preferably 74.0 mol % to 89.0 mol % (e.g., 80.0 to 89.0 mol % etc.) and particularly preferably 85.0 mol % to 89.0 mol % (e.g., 85.5 to 89.0 mol %, 86.0 to 89.0 mol %, 86.5 to 89.0 mol %, 87.0 to 89.0 mol %, 87.5 to 88.9 mol %, or 88.0 to 88.8 mol %) for fast dissolution in a living body.

When the average saponification value is 85.0 mol % or more, the PVA-based polymer can be used as a material of pharmaceutical preparations adapted for global markets. In addition, the proportion of hydrophobic groups in such a PVA-based polymer is low enough so that the PVA-based polymer is highly hydrophilic, less likely to precipitate at high temperature in preparing an aqueous solution, and easy to handle. That is why the lower limit specified above is particularly preferred.

Similarly, when the average saponification value is 89.0 mol % or less, the PVA-based polymer can be used as a material of pharmaceutical preparations adapted for global markets. In addition, since the proportion of hydroxyl groups in PVA is not so high, the reduction in water solubility due to high crystallinity and the disintegrability and dissolution rate of the tablet fall into a proper range. That is why the upper limit specified above is particularly preferred.

The method for measuring the average saponification value of PVA is not particularly limited, and for example, the method for measuring the saponification value specified in JIS K6726 can be used.

In the present invention, a PVA-based polymer having a specific saponification value distribution is used.

More specifically, the PVA-based polymer meets the following requirement (A).

Requirement (A):

Based on data obtained by measurement of the polyvinyl alcohol-based polymer by liquid chromatography, a value represented by formula (3) shown below is 22 or more,
wherein the measurement is performed with a liquid chromatography system equipped with a charged aerosol detector and a Thermo Scientific Acclaim™ 300 column (catalog number: 060266, carbon load: 8%, maximum pressure: 4500 psi, particle size: 3 μm, pore size: 300 Å, stationary phase: C18, surface area: 100 m²/g, length: 150 mm, diameter: 4.6 mm, pH: 2.5 to 7.5, material: glass lined tubing) under the measurement conditions described below,
wherein the data represent a baseline-normalized intensity over a retention time of 5.0 to 12.0 minutes at a sampling interval of 500 ms, and
wherein the value represented by formula (3) is calculated from formulae (1) and (2) shown below, wherein the intensity at a retention time $T_i$ [min] is represented by $P_i$ [pA].

Measurement Conditions

Concentration of an aqueous polyvinyl alcohol-based polymer solution: 0.1% by mass Injection volume of the aqueous polyvinyl alcohol-based polymer solution: 2 μL
Column temperature: 50° C.
Flow rate: 1.0 mL/min
Eluent: a mixed solvent of water and methanol
Eluent gradient conditions: the ratio of water and methanol in the eluent changes from 95:5 to 15:85 at a constant rate over a run time from minutes 0 to 10; and the ratio of water and methanol in the eluent is constant at 15:85 over a run time from minutes 10 to 15.

Formulae $T_n = \Sigma(T_i \times P_i)/\Sigma(P_i)$     Formula (1)

$T_w = \Sigma(T_i^2 \times P_i)/\Sigma(T_i \times P_i)$     Formula (2)

$\{(T_w/T_n) - 1\} \times 1000$     Formula (3)

In the requirement described above, the charged aerosol detector and liquid chromatography system used are not particularly limited. For example, the charged aerosol detector used may be Thermo Scientific CORONA VEO, and the liquid chromatography system used may be Thermo Scientific ULTIMATE 3000.

When the PVA-based polymer is measured with a liquid chromatography system equipped with a charged aerosol detector, inside of the charged aerosol detector, a sample solution containing the PVA eluted from the column is sprayed and dried in nitrogen to form atomized particles, and atomized PVA particles are charged with $N^+$ ions and detected by an electrometer.

The column used in the liquid chromatography system of the present invention is usually a Thermo Scientific Acclaim™ 300 column (catalog number: 060266, carbon load: 8%, maximum pressure: 4500 psi, particle size: 3 μm, pore size: 300 Å, stationary phase: C18, surface area: 100 m²/g, length: 150 mm, diameter: 4.6 mm, pH: 2.5 to 7.5, material: glass lined tubing), a reverse-phase ODS column in which a porous spherical silica gel chemically surface-modified with octadecylsilyl groups is packed as a stationary phase.

The analytical sample, namely, the PVA-based polymer is dissolved in purified water and measured in an aqueous solution. The concentration of the PVA-based polymer in the aqueous solution is usually 0.1% by mass.

The measurement conditions are usually as follows: the flow rate is 1 mL/min; the column temperature is 50° C.; and the injection volume of the aqueous PVA-based polymer solution is 2 μL.

The eluent used is usually a mixed solvent of water and methanol.

The measurement is usually performed under eluent gradient conditions.

The eluent gradient conditions over a run time are usually as follows: the ratio of water and methanol in the eluent is 95:5 at minute 0; the ratio of water and methanol in the eluent changes at a constant rate (e.g., the ratio of water to methanol is reduced by 8 per minute while the ratio of methanol to water is increased by 8 per minute) over a run time from minutes 0 to 10 to reach 15:85 at minute 10; and the ratio of water and methanol in the eluent is constant at 15:85 over a run time from minutes 10 to 15.

During a time period for which the water ratio in the eluent is higher, a high-saponified PVA component in the PVA-based polymer is eluted; and as the methanol ratio increases, a low-saponified PVA component in the PVA-based polymer is gradually eluted.

If a dead space is present in the column, the gradient elution from minutes 0 to 10 may be insufficient to achieve accurate measurement. In order to prevent this problem, the eluent is usually passed for 5 minutes under the above conditions.

After 15 minutes, preferably, an eluent composed of water and methanol at a ratio of 5:95 is passed for 5 minutes to flush out the remaining low-saponified PVA component from the column. When another PVA-based polymer is successively measured, it is preferable that an eluent composed of water and methanol at a constant ratio of 95:5 is passed for about 7 to 10 minutes to re-equilibrate the column to the initial conditions.

From the measurement of the PVA-based polymer sample under the above conditions, a graph showing the relationship between the intensity versus the retention time can be obtained. The data in the graph are normalized by subtraction of the baseline obtained from the measurement under the same measurement conditions without loading the sample, thus resulting in a graph plotting the baseline-normalized intensity against the retention time.

FIG. 1 is a chart plotting the intensity over a retention time of 5.0 to 12.0 minutes from the data obtained by the measurement of a PVA (manufactured by JAPAN VAM & POVAL CO., LTD., JP-05) having an average saponification value of 88.2 mol % and a 4% by mass aqueous solution viscosity of 5.3 mPa·s, each of which was measured according to JIS K6726.

In the present invention, the intensity data are obtained at a sampling interval of preferably 500 ms (that is, 0.5 second), more preferably less than 2 seconds. Here, the sampling interval is the frequency at which a data processor receives the signals transmitted from the detector. The thus-obtained data are plotted to give a chart as shown in FIG. 1.

Under the liquid chromatography conditions used in the present invention, the elution of the high-saponified PVA component in the PVA-based polymer sample is predominant at early stages of the measurement using an eluent with a high water ratio, and the elution of the low-saponified PVA component increases with the increase in methanol ratio in the eluent, as described above. For this reason, in the chart plotting the ion intensity against the retention time from the data obtained by a corona detector, a sharp peak centered at a retention time of around 9.5 minutes appears in the measurement of a PVA-based polymer with a narrow saponification value distribution, while a broad peak centered at the same retention time appears in the measurement of a PVA-based polymer with a broad saponification value distribution even when the two PVA-based polymers have the same saponification value.

In the obtained data on the intensity versus the retention time, when the intensity at a retention time $T_i$ [min] is represented by $P_i$ [pA], $T_n$ and $T_w$ can be represented by formula (1) and formula (2), respectively. Here, $T_n$ and $T_w$ correspond to number-average molecular weight $M_n$ and weight-average molecular weight $M_w$, respectively, in the molecular weight distribution measurement using gel permeation chromatography (hereinafter referred to as GPC).

Similarly, $T_w/T_n$ corresponds to the so-called dispersity $M_w/M_n$ in the molecular weight distribution measurement. Therefore, the degree of saponification value distribution can be represented by formula (3).

The value represented by formula (3) (namely, $\{(T_w/T_n)-1\} \times 1000$) is 22 or more (e.g., 23 or more), for example, 25 or more (e.g., 27 or more), preferably 28 or more (e.g., 30 or more), more preferably 32 or more (e.g., 33 or more), and may be 35 or more (e.g., 38 or more, 40 or more, 42 or more, 44 or more, or the like).

The upper limit of the value represented by formula (3) is not particularly specified and may be, for example, 100, 98, 95, 93, 90, 88, 85, 83, 80, 78, 75, or the like.

The viscosity of a 4% by mass aqueous solution of the PVA-based polymer (as measured according to JIS K6726) is not particularly limited. The viscosity is preferably 2.0 to 10.0 mPa·s (e.g., 2.2 to 9.5 mPa·s, 2.5 to 9.0 mPa·s, or 2.8 to 8.5 mPa·s) and may be 3.0 to 7.0 mPa·s or less (e.g., 3.5 to 6.5 mPa·s, 4.0 to 6.0 mPa·s, or 4.5 to 5.5 mPa·s).

When the 4% by mass aqueous solution has such a viscosity and the above-described requirement (A) is met, shorter disintegration time of tablets is efficiently and easily achieved.

The PVA-based polymer used may be obtained commercially or synthesized. The method for producing the PVA-based polymer is not particularly limited, and known methods, for example, saponification of a polymer containing a vinyl ester monomer as a polymerizable component (vinyl ester-based polymer), may be used.

The vinyl ester monomer is not particularly limited, and examples include fatty acid vinyl esters [e.g., $C_{1-20}$ fatty acid vinyl esters (e.g., $C_{1-16}$ alkanoic acid vinyl esters) such as vinyl formate, vinyl acetate, vinyl propionate, vinyl butyrate, vinyl caprylate, vinyl versatate, and vinyl monochloroacetate], and aromatic carboxylic acid vinyl esters [e.g., vinyl arenecarboxylates (e.g., $C_{7-12}$ arene carboxylic acid vinyl esters) such as vinyl benzoate].

One kind of vinyl ester monomer or a combination of two or more kinds of vinyl ester monomers may be used.

The vinyl ester monomer preferably at least contains a fatty acid vinyl ester (e.g., $C_{1-10}$ alkanoic acid vinyl esters etc., such as vinyl formate, vinyl acetate, vinyl propionate, and vinyl butyrate). Particularly, vinyl acetate is preferred from industrial or other viewpoints.

The vinyl ester-based polymer has a vinyl ester unit, and if necessary, may have an additional monomer unit (a monomer capable of copolymerizing with vinyl ester monomers) (in other words, the vinyl ester-based polymer may be modified with an additional monomer).

The additional monomer is not particularly limited, and examples include, but are not limited to, α-olefins (e.g., ethylene, propylene, etc.), (meth)acrylic acid esters [e.g., (meth)acrylic acid alkyl esters such as methyl (meth)acrylate, ethyl (meth)acrylate, butyl (meth)acrylate, and 2-ethylhexyl (meth)acrylate], unsaturated amides [e.g., (meth) acrylamide, diacetone acrylamide, N-methylolacrylamide, etc.], unsaturated acids {e.g., unsaturated acids [e.g., (meth) acrylic acid, crotonic acid, maleic acid, itaconic acid, fumaric acid, etc.], unsaturated acid esters [unsaturated acid esters other than (meth)acrylic acid esters, e.g., alkyl (methyl, ethyl, propyl, etc.) esters etc.], unsaturated acid anhydrides (maleic anhydride etc.), salts of unsaturated acids [e.g., alkali metal salts (e.g., sodium salts, potassium salts, etc.), ammonium salts, etc.], etc.}, glycidyl group-containing monomers [e.g., allyl glycidyl ethers, glycidyl (meth)acrylate, etc.], sulfonic group-containing monomers (e.g., 2-acrylamide-2-methylpropane sulfonic acid, salts thereof, etc.), phosphate group-containing monomers [e.g., acid phosphoxy ethyl (meth)acrylate, acid phosphoxy propyl (meth)acrylate, etc.], vinyl ethers (e.g., alkyl vinyl ethers), allyl alcohols, etc.

One kind of additional monomer or a combination of two or more kinds of additional monomers may be used.

In the case where the additional monomer is contained as a polymerizable component in the vinyl ester-based polymer, the proportion of the additional monomer in the polymerizable components may be, for example, 50% by mass or less, 30% by mass or less, 20% by mass or less, or 10% by mass or less.

The proportion of the vinyl ester monomer in the polymerizable components is, for example, 50% by mass or more, preferably 70% by mass or more, more preferably 90% by mass or more and may be 100% by mass.

In the PVA-based polymer, some vinyl alcohol units may be modified by a reaction, such as acetalization, etherification, acetoacetylization, or cationization.

The method for polymerizing the polymerizable components (e.g., the polymerizable components including the vinyl ester monomer such as vinyl acetate) is not particularly limited, and examples include known polymerization methods such as block polymerization, solution polymerization, suspension polymerization, and emulsion polymerization. Among them, solution polymerization using methanol as a solvent is industrially preferred. In the solution polymerization, known initiators such as peroxide initiators and azo initiators can be used, and the polymerization degree of the vinyl ester-based polymer can be adjusted by varying the feed ratio of the polymerizable components and methanol and the polymerization yield. For the production of the PVA-based polymer, commercial vinyl ester-based polymers (polyvinyl acetate resin etc.) can be used as a starting material.

The method for saponifying the vinyl ester-based polymer (e.g., polyvinyl acetate) can be a conventional saponification method using an alkaline or acid catalyst. In particular, industrially preferred is alcoholysis, which is performed by adding an alkali such as sodium hydroxide to a solution of the vinyl ester-based polymer (e.g., polyvinyl acetate) in methanol or in a mixed solvent of methanol, water, methyl acetate, etc. and stirring the mixture for cleavage of the acyl group (e.g., acetyl group) of the vinyl ester-based polymer (e.g., polyvinyl acetate).

After that, the obtained mass product, gelled product, or granular product is pulverized, and if needed, the alkali is neutralized; then the solid is separated from the liquid and dried to yield a PVA-based polymer.

The PVA-based polymer used in the present invention can efficiently be produced by performing saponification in a less homogenous system than usual. For such saponification, the following approaches can be employed: saponification is performed using a methanol solution of the vinyl ester-based polymer (e.g., polyvinyl acetate) at a higher concentration (e.g., 55% by mass or more); saponification is performed with stirring at a lower speed (e.g., 20 rpm or less) after addition of an alkali; saponification is performed for a shorter time for mixing and stirring after the addition of an alkali; saponification is performed using a larger amount of an alkali for a shorter time; and saponification is performed in a reaction system having a temperature gradient or distribution created by, for example, adjusting the temperatures of a methanol solution of the vinyl ester-based polymer (e.g., polyvinyl acetate) and an alkali to be added to the solution.

Other approaches are available, and for example, saponification may be performed under the conditions that the solvents added, such as water and methyl acetate, are in a less homogenous state, in view of the fact that the homogeneity of the solvents affects the saponification speed. These approaches easily achieve the variation in saponification value in the PVA-based polymer after saponification.

This means that the PVA-based polymer produced by any of these approaches has the same average saponification value as that of the PVA-based polymer produced by the conventional method but a broader saponification value distribution.

In addition to the above-described approaches, for a broader saponification value distribution, two or more types of PVAs having different saponification values may be blended such that the weighted average saponification value falls into the desired value. This can be used as one embodiment of the PVA-based polymer in the present invention.

In this case, the PVA-based polymer can be obtained by mixing a plurality of types of PVAs, for example, two different PVAs, PVA (a) and PVA (b).

The average saponification value of the PVA (a) as measured according to the method for measuring the saponification value specified in JIS K6726 is, for example, 85 mol % or more (e.g., 85 to 99 mol %), preferably 88 mol % or more (e.g., 88 to 99 mol %), more preferably 90 mol % or more (e.g., 90 to 99 mol %), and still more preferably 92 mol % or more (e.g., 92 to 99 mol %).

The average saponification value of the PVA (b) as measured in the same manner as above is, for example, 99 mol % or less (e.g., 60 to 99 mol %), preferably 95 mol % or less (e.g., 60 to 95 mol %), more preferably 90 mol % or less (e.g., 65 to 90 mol %), and still more preferably 88 mol % or less (e.g., 65 to 88 mol %).

The ratio of PVA (a) and PVA (b) can be selected depending on the value of formula (3) etc. The mass ratio of PVA (a):PVA(b) is, for example, 5:95 to 95:5, preferably 10:90 to 90:10, more preferably 15:85 to 85:15, and still more preferably 20:80 to 80:20.

The weighted average saponification value of the PVA-based polymer obtained by mixing PVA (a) and PVA (b) (when the saponification value of PVA (a) is A mol %, the saponification value of PVA (b) is B mol %, and the ratio of PVA (a) and PVA (b) is A':B', the weighted average saponification value C is expressed as $C=(A\times A'+B\times B')/100$) can be selected from the same range as described above and is, for example, 83.0 to 89.0 mol %, preferably 85.0 to 89.0 mol %, more preferably 86.0 to 89.0 mol %.

Binder Etc.

The binder of the present invention comprises the PVA-based polymer.

As long as the binder of the present invention functions as a binder for a substance to be mixed therewith (e.g., a powder), the application of the binder is not particularly limited, but the binder is particularly suitable for use as a binder for granulation.

The substance to be mixed with the binder is not particularly limited and may be, for example, a pharmaceutical product, a quasi-pharmaceutical product, a food product, or the like. The substance to be mixed with the binder may be an active ingredient, a nutrient (or nutritional ingredient), or the like, and may be a medicinal substance (an active pharmaceutical ingredient etc.).

The substance to be mixed with the binder may be an organic substance or an inorganic substance, a mixture thereof, or an organic-inorganic hybrid material.

The medicinal substance or the active ingredient (or the medicinal substance or the active ingredient contained in the substance to be mixed with the binder) is not particularly limited. Examples of the medicinal substance include central nervous system drugs, cardiovascular drugs, respiratory drugs, gastrointestinal drugs, antibiotics, antitussives and expectorants, antihistamines, antipyretic, analgesic, and antiphlogistic drugs, diuretics, autonomic drugs, antimalarials, antidiarrheals, psychotropics, and vitamins and derivatives thereof.

Examples of the central nervous system drug include diazepam, idebenone, aspirin, ibuprofen, paracetamol, naproxen, piroxicam, indomethacin, sulindac, lorazepam, nitrazepam, phenytoin, acetaminophen, ethenzamide, ketoprofen, and chlordiazepoxide.

Examples of the cardiovascular drug include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, propranolol hydrochloride, and alprenolol hydrochloride.

Examples of the respiratory drug include amlexanox, dextromethorphan, theophylline, pseudoephedrine, salbutamol, and guaifenesin.

Examples of the gastrointestinal drug include benzimidazole drugs with antiulcer activity, such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole, cimetidine, ranitidine, pirenzepine hydrochloride, pancreatin, bisacodyl, and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, dextromethorphan hydrobromide, isoaminile citrate, and dimemorfan phosphate.

Examples of the antihistamine include chlorpheniramine maleate, diphenhydramine hydrochloride, and promethazine hydrochloride.

Examples of the antipyretic, analgesic and antiphlogistic drug include ibuprofen, diclofenac sodium, flufenamic acid, sulpyrine, aspirin, and ketoprofen.

Examples of the diuretic include caffeine.

Examples of the autonomic drug include dihydrocodeine phosphate, dl-methylephedrine hydrochloride, atropine sulfate, acetylcholine chloride, and neostigmine.

Examples of the antimalarial include quinine hydrochloride.

Examples of the antidiarrheal include loperamide hydrochloride.

Examples of the psychotropic include chlorpromazine.

Examples of the vitamin and a derivative thereof include vitamin A, vitamin B1, fursultiamine, vitamin B2, vitamin B6, vitamin B12, vitamin C, vitamin D, vitamin E, vitamin K, calcium pantothenate, and tranexamic acid.

In the case where the substance to be mixed with the binder contains an active ingredient, a nutrient, etc., the substance to be mixed with the binder may further contain an additional ingredient (any additive usually used in this field, for example, a filler, a disintegrant, a lubricant, an antiagglomerant, a solubilizer, etc.).

Examples of the filler include saccharides, such as sucrose, lactose, mannitol, and glucose, starch, crystalline cellulose, calcium phosphate, calcium sulfate, etc. Examples of the disintegrant include low-substituted hydroxypropyl cellulose, carmellose or a salt thereof, croscarmellose sodium, sodium carboxymethyl starch, crospovidone, microcrystalline cellulose, microcrystalline cellulose-carmellose sodium, etc. Examples of the lubricant or the antiagglomerant include talc, magnesium stearate, calcium stearate, colloidal silica, stearic acid, waxes, hydrogenated oils, polyethylene glycols, sodium benzoate, etc. Examples of the solubilizer include organic acids, such as fumaric acid, succinic acid, malic acid, and adipic acid, etc. One of these additives or two or more of them may be used. The amount of the additional ingredient (the additive) can be determined as appropriate according to, for example, the type of the drug.

One kind of substance to be mixed with the binder or a combination of two or more kinds of substances to be mixed with the binder may be used.

The substance to be mixed with the binder may be a solid at ordinary temperature (e.g., 10 to 40° C. etc.).

The substance to be mixed with the binder may be, for example, in the form of powder (or powder particles). The particle size of the powder (active ingredient, active ingredient powder, etc.) is not particularly limited, and the average particle diameter is, for example, about 500 µm or less (e.g., 5 to 400 µm), preferably about 300 µm or less, more preferably about 100 µm or less (e.g., 10 to 80 µm).

The average particle diameter of the powder may be measured with a laser-type particle size distribution measuring instrument etc.

In the case where the binder is used for granulation, granulated materials (granular powder) can be obtained. That is, the granulated material comprises a substance to be mixed with the binder (powder particles etc.) and the binder. In other words, the granulated material can also be called a granulated material in which the binder is the binder of the present invention (or the polyvinyl alcohol-based polymer).

A powdery granulated material (granular powder) may usually be in the form of a granule (granular shape).

The particle size of the granulated material (e.g., granules) can be determined as appropriate according to the size of the powder particles, the granulation method, etc. The average particle diameter is, for example, about 700 µm or less (e.g., 30 to 600 µm), preferably about 400 µm or less, and more preferably about 300 µm or less (e.g., 50 to 200 µm).

The average particle diameter of the granulated material may be measured with a laser-type particle size distribution measuring instrument etc.

The proportion of the binder (or the polyvinyl alcohol-based polymer) in the granulated material can be selected from the range of, for example, about 0.1 to 50% by mass, may be about 0.2 to 30% by mass (e.g., 0.3 to 15% by mass), and is preferably about 0.5 to 10% by mass (e.g., 0.7 to 8% by mass), more preferably about 1 to 5% by mass (e.g., 1 to 3% by mass).

The proportion of the binder (or the polyvinyl alcohol-based polymer) of the present invention in the granulated material can be selected from the range of, for example, about 0.001 to 0.5 part by mass relative to 1 part by mass of the powder particles, may be about 0.002 to 0.2 part by mass (e.g., 0.003 to 0.15 part by mass), and is preferably about 0.005 to 0.1 part by mass (e.g., 0.007 to 0.08 part by mass), more preferably about 0.01 to 0.05 part by mass (e.g., 0.01 to 0.03 part by mass).

The binder of the present invention is not particularly limited in usage as long as it functions as a binder for the substance to be mixed therewith. Usually, the binder of the present invention is used by contact with the substance to be mixed therewith.

In particular, by using the binder (or the polyvinyl alcohol-based polymer) of the present invention for granulation (bringing the binder into contact with the substance to be mixed therewith), a granulated material can be produced.

The use of the binder (the granulated material) of the present invention optionally includes the following embodiments (1) to (3):
(1) use for levodopa and/or carbidopa (e.g., incorporation a polymer mixture composed of polyvinyl alcohols having different saponification values into a levodopa or carbidopa-containing pharmaceutical preparation);
(2) use for irbesartan (e.g., incorporation into an irbesartan-containing pharmaceutical composition); and
(3) use for obeticholic acid or a pharmaceutically acceptable salt thereof (e.g., use as a water-soluble polymer binder (corresponding to (iii) below) in an oral pharmaceutical preparation containing obeticholic acid or a pharmaceutically acceptable salt thereof, (i) a water-soluble filler, (ii) a disintegrant, and (iii) a water-soluble polymer binder.

The granulation method is not particularly limited, and dry granulation (e.g., powder (such as medicinal substance powder) and a binder are mixed, the powder mixture is compacted by applying a force with an apparatus called a roller compactor to form larger particles, and the particles are ground to produce granules) may be used. Typically, wet granulation may be used.

Wet granulation at least includes a step of bringing the binder in a liquid form into contact with the substance to be mixed therewith (granulation step). In a typical granulation step, the binder (or the polyvinyl alcohol-based polymer) may be brought into contact with the substance to be mixed therewith in the presence of a solvent. More specifically, a dispersion or solution (in particular, an aqueous and/or water-based solution) containing the binder may be brought into contact with (e.g., sprayed onto or added dropwise onto) the substance to be mixed therewith (in particular, powder particles) (e.g., solution addition method). Alternatively, a solvent (a solvent which can dissolve or disperse the binder) may be brought into contact with (e.g., sprayed onto or added dropwise onto) a mixture of the binder and the substance to be mixed therewith (powder particles) (e.g., powder addition method).

The solvent is not particularly limited as long as it can dissolve or disperse the binder (or the polyvinyl alcohol-based polymer). Usually, water or a mixed solvent (water-based solvent) of water and an organic solvent is suitable, and in particular, water or a water-based solvent (typically water) is preferably suitable. The organic solvent (water-miscible solvent) is not particularly limited, and examples include alcohols (e.g., ethanol etc.) etc.

In the wet granulation, the proportion or the amount of the solvent used (e.g., the proportion of water in an aqueous solution) is, for example, about 1 to 70 parts by mass (e.g., 3 to 60 parts by mass), preferably about 4 to 50 parts by mass (e.g., 5 to 45 parts by mass), and more preferably about 7 to 40 parts by mass (e.g., 8 to 35 parts by mass) relative to 100 parts by mass of the substance to be mixed with the binder (powder particles).

Specific examples of the wet granulation include fluid bed granulation, high-speed stirring granulation, extrusion granulation, tumbling granulation, etc. In particular, fluid bed granulation, high-speed stirring granulation, etc. are suitable in the present invention.

Fluid bed granulation is performed, for example, in the following procedure: the substance to be mixed with the binder (powder) is fed into a layer called a fluid bed; and while warm air flow is supplied from the bottom to fluidize the substance to be mixed with the binder (powder), a solution or dispersion (in particular, an aqueous solution) containing the binder is sprayed from the above to form granules. In fluid bed granulation, drying is performed concomitantly with granulation (a step of forming granules), and the time of drying can be saved after granulation.

For high-speed stirring granulation, a high-speed stirring granulator with a large blade called a blender and a small blade called a chopper inside of the apparatus is used, for example. In such high-speed stirring granulation, the substance to be mixed with the binder (powder) is fed into the apparatus, and while the stirring blades are rotated, a solution or dispersion (in particular, aqueous solution) containing the binder is sprayed or added dropwise to form granules. After granulation, drying is performed and thus finished granules are obtained.

The granulated material (e.g., granules) can be used in various ways according to the type of the substance to be mixed with the binder, the desired application, etc. For example, the granulated material may be directly used as granules (e.g., granules, granules in a capsule, etc.) or molded into any form.

For example, the granulated material (granules) can be used as a material for tablets. In other words, such a tablet contains the granulated material and can be produced from the granulated material by tableting.

The granulated material (and a molded product therefrom such as a tablet) of the present invention is suitable for oral application (oral preparations).

The tablet contains at least the granulated material and optionally an additional ingredient.

The additional ingredient may be any additive usually used in this field (e.g., a disintegrant, a lubricant, an antiagglomerant, a solubilizer, etc.).

Examples of the disintegrant include low-substituted hydroxypropyl cellulose, carmellose or a salt thereof, croscarmellose sodium, sodium carboxymethyl starch, crospovidone, microcrystalline cellulose, microcrystalline cellulose-carmellose sodium, etc.

Examples of the lubricant or the antiagglomerant include talc, magnesium stearate, calcium stearate, colloidal silica, stearic acid, waxes, hydrogenated oils, polyethylene glycols, sodium benzoate, etc.

Examples of the solubilizer include organic acids, such as fumaric acid, succinic acid, malic acid, and adipic acid, etc.

One of these additives or two or more of them may be used.

The amount of the additive can be determined as appropriate according to, for example, the kind(s) of the ingredient(s) contained in the tablet or in the granulated material.

The proportion of the binder (or the polyvinyl alcohol-based polymer) in the tablet is, for example, about 0.5 to 10% by mass, preferably about 2 to 6% by mass (e.g., 1 to 5% by mass), more preferably about 1 to 3% by mass and may be 3% by mass or less (e.g., 1 to 2% by mass, 2 to 3% by mass, etc.).

The shape of the tablet is not particularly limited and may be any shape, such as a disk shape, a lens shape, or a pole shape.

The size of the tablet is also not particularly limited and may be, for example, 3 mm or more (e.g., 4 to 15 mm, 5 to 12 mm, 8 to 11 mm, etc.) in diameter (maximum diameter).

The tableting method is not particularly limited, and conventional tableting methods can be employed.

The tablet may have a coat layer on the surface of the tablet. Therefore, the present invention further includes a coated tablet comprising a tablet and a coat layer (coating layer) coating a surface of the tablet.

The component of the coat layer in the coated tablet is not particularly limited, and examples include resin materials, such as cellulose resin (e.g., hydroxypropylmethyl cellulose, hydroxypropylmethylcellulose acetate succinate etc.), and polyvinyl alcohol-based polymers.

In the case where the coat layer comprises a polyvinyl alcohol-based polymer, the polyvinyl alcohol-based polymer optionally but preferably meets the above-described requirement (A). In the case where the coat layer is composed of a polyvinyl alcohol-based polymer which meets requirement (A), the coat layer can be formed in an efficient and highly productive manner, prevent adhesion between tablets, and provide moisture-proofing and gas barrier properties.

The method for forming the coat layer on the surface of the tablet (the method for producing the coated tablet) is not particularly limited, and known types of coating, for example, film coating etc. may be used.

The coating technique may be, for example, spray coating.

The coating apparatus used may be, for example, a pan coater, a drum coater, or the like. These apparatuses may be equipped with an air spray, an airless spray, or other types of spray devices.

A specific example of the method for forming the coat layer is given below. A coating composition which contains the components of the coat layer, and if necessary, an additive, is dissolved or dispersed in a solvent [e.g., water, an organic solvent (e.g., an alcohol such as ethanol etc.), a mixed solvent of water and an organic solvent, etc.] to prepare a coating composition solution, and the solution is sprayed or applied to a tablet using the above-mentioned coating apparatus in parallel with drying to coat the surface of the tablet.

The coating weight of the coating composition for coating the surface of the tablet varies with the type, form, size, and surface condition of the tablet, the properties of the components and additives contained in the tablet, and other factors. For example, the coating weight is preferably 1 to 10% by mass, more preferably 1 to 7% by mass, and particularly preferably 2 to 6% by mass relative to the total weight of the tablet. When the coating weight is within this range, perfect coating is achieved, and sufficient moisture-proofing, oxygen barrier, and odor masking are provided. In addition, the time for coating is shortened. That is why the range specified above is preferred.

The coated tablet may have a multi-layered structure having the coat layer and an additional layer. The additional layer may be, for example, an undercoat layer (a layer formed on the lower surface of the coat layer) and/or an overcoat layer (a layer formed on the upper surface of the coat layer). The additional layer can also be composed of the same components as those of the coat layer.

EXAMPLES

Hereinafter, the present invention will be described in more detail by examples, but the present invention is not limited thereto.

In the following Examples and Comparative Examples, "percentage (%)" and "part" are on a mass basis unless otherwise specified.

The experimental conditions are as follows.
Average Saponification Value and 4% by Mass Aqueous Solution Viscosity The measurements were performed according to JIS K6726.
Confirmation of Whether or not Requirement (A) is Met
Liquid Chromatography Measurement Conditions
  Detector: charged aerosol detector
  Column: Thermo Scientific, Acclaim™ 300 (catalog number: 060266, carbon load: 8%, maximum pressure:

4500 psi, particle size: 3 μm, pore size: 300 Å, stationary phase: C18, surface area: 100 m²/g, length: 150 mm, diameter: 4.6 mm, pH: 2.5 to 7.5, material: glass lined tubing)

Concentration of an aqueous PVA-based polymer solution: 0.1% by mass

Injection volume of the aqueous PVA-based polymer solution: 2 μL

Column temperature: 50° C.

Flow rate: 1.0 mL/min

Eluent: a mixed solvent of water and methanol

Eluent gradient conditions: the ratio of water and methanol in the eluent changes from 95:5 to 15:85 at a constant rate (e.g., the ratio of water to methanol is reduced by 8 per minute while the ratio of methanol to water is increased by 8 per minute) over a run time from minutes 0 to 10; and the ratio of water and methanol in the eluent is constant at 15:85 over a run time from minutes 10 to 15.

After the measurement of the PVA-based polymer by liquid chromatography under the above conditions, the data representing a baseline-normalized intensity over a retention time of 5.0 to 12.0 minutes at a sampling interval of 500 ms were used to calculate a value represented by formula (3) based on $T_n$ represented by formula (1) and $T_w$ represented by formula (2), wherein the intensity at a retention time $T_i$ [min] is represented by $P_i$ [pA].

Formulae $$T_n = \Sigma(T_i \times P_i)/\Sigma(P_i) \quad \text{Formula (1)}$$

$$T_w = \Sigma(T_i^2 \times P_i)/\Sigma(T_i \times P_i) \quad \text{Formula (2)}$$

$$\{(T_w/T_n) - 1\} \times 1000 \quad \text{Formula (3)}$$

Granulation Conditions
  Granulator: MP-01 (Powrex)
  Inlet air temperature: 55 to 64° C.
  Outlet air temperature: 28 to 34° C.
  Inlet air flow: 0.8 to 1.0 m³/min
  Spray air flow: 35 L/min
  Spray air pressure: 0.11 MPa
  Amount of aqueous binder solution: 250 g
  Concentration of aqueous binder solution: 4 wt %
  Drying conditions after granulation: after the completion of granulation, drying is performed until the outlet temperature reaches 40° C.

Tableting Conditions
  Tablet press: VERGO (manufactured by KIKUSUI SEISAKUSHO LTD.)
  Tableting pressure: 10 kN
  Tablet press rotational speed: 10 rpm
  Tablet weight: 200 mg Evaluation of Tablet Hardness The hardness of the obtained tablet was measured using a tablet hardness tester (TBH125 manufactured by ERWEKA). The measurement was performed 6 times and the average value of the 6 results was used as the measured value.

Evaluation of Disintegration Time

The disintegration time of the obtained tablet was measured using a disintegration tester (NT400 manufactured by Toyama Sangyo Co., Ltd.). For the measurement, the disintegration test method of the Japanese Pharmacopoeia was used as a test method, and pure water (purified water) was used as a test medium. The measurement was performed 6 times and the average value of the 6 results was used as the measured value.

Synthesis Methods of PVA-Based Polymers

Comparative Synthesis Example 1

A commercial polyvinyl acetate resin (manufactured by JAPAN VAM & POVAL CO., LTD., JMR-30LL, polymerization degree: 590) was dried in vacuo at 100° C. for water removal. This was dissolved in methanol to prepare a 46% by mass methanol solution of polyvinyl acetate. For saponification, 500 parts by mass of this solution was heated to 40° C., and 16 parts by mass of a 3% by mass methanol solution of sodium hydroxide adjusted to 35° C. was added. The mixture was stirred using a propeller-type blade at 300 rpm for 1 minute and then allowed to stand at 40° C. for 40 minutes. The obtained gelled material was ground and soaked in a mixed solvent composed of 570 parts by mass of methanol, 230 parts by mass of methyl acetate, and 17 parts by mass of water. With gentle stirring, saponification was further performed at 40° C. for 1 hour. The reaction mixture was neutralized to a pH of 8 to 9 with a 1% by mass aqueous acetic acid solution. The solid was separated from the liquid and dried at 60° C. for 8 hours to give a PVA-based polymer.

The measured physical properties of the obtained PVA-based polymer are shown in Table 1.

Comparative Synthesis Example 2

Six parts by mass of a commercial PVA resin (manufactured by JAPAN VAM & POVAL CO., LTD., JL-05E, saponification value: 80.2 mol %, viscosity of 4% by mass aqueous solution: 5.1 mPa·s) and 94 parts by mass of a commercial PVA resin (manufactured by JAPAN VAM & POVAL CO., LTD., JP-05, saponification value: 88.0 mol %, viscosity of 4% by mass aqueous solution: 5.3 mPa·s) were placed into a polyethylene bag. The bag was shaken about 100 times so that the PVA powders were mixed into a homogeneous mixture. Thus, a PVA-based polymer (a mixture of 2 types of PVA-based polymers) was prepared.

The measured physical properties of the obtained PVA-based polymer are shown in Table 1.

Synthesis Example 1

A PVA-based polymer was obtained in the same manner as described in Comparative Synthesis Example 1 except that the mixture of the methanol solution of polyvinyl acetate and the sodium hydroxide solution was stirred at a speed of 60 rpm for 30 seconds, that is, stirring was performed under the conditions to keep the mixture less homogeneous than usual.

The measured physical properties of the obtained PVA-based polymer are shown in Table 1.

Synthesis Example 2

A PVA-based polymer was obtained in the same manner as described in Comparative Synthesis Example 1 except that the mixture of the methanol solution of polyvinyl acetate and the sodium hydroxide solution was stirred at a speed of 20 rpm for 60 seconds, that is, stirring was performed under the conditions to keep the mixture less homogeneous than usual.

The measured physical properties of the obtained PVA-based polymer are shown in Table 1.

Synthesis Example 3

A PVA-based polymer was obtained in the same manner as described in Comparative Synthesis Example 1 except that saponification was performed using a mixture of 500 parts by mass of a 55% by mass methanol solution of polyvinyl acetate and 23 parts by mass of the sodium hydroxide solution.

The measured physical properties of the obtained PVA-based polymer are shown in Table 1.

Synthesis Example 4

A PVA-based polymer was obtained in the same manner as described in Comparative Synthesis Example 1 except that saponification was performed with the following changes: a band heater was wrapped around the upper half of the vessel containing the mixture of the methanol solution of polyvinyl acetate and the sodium hydroxide solution to heat the upper half to 50° C., so that a temperature gradient in which the temperature of the upper half was 50° C. and the temperature of the lower half was room temperature (25° C.) was applied during the reaction; and the mixture was allowed to stand for 50 minutes.

The measured physical properties of the obtained PVA-based polymer are shown in Table 1.

Synthesis Example 5

A PVA-based polymer was obtained in the same manner as described in Comparative Synthesis Example 1 except for the following changes: 500 parts by mass of the 46% by mass methanol solution of polyvinyl acetate was equally divided into two portions (250 parts by mass each) in separate vessels, which portions were heated to 40° C.; for saponification, 10 parts by mass of the 3% by mass methanol solution of sodium hydroxide adjusted to 35° C. was added to one portion, 6 parts by mass of the sodium hydroxide solution was added to the other portion, and both the mixtures were separately and simultaneously stirred at 300 rpm for 1 minute and then allowed to stand at 40° C. for 40 minutes; and the separately obtained gelled materials were combined together and ground.

The measured physical properties of the obtained PVA-based polymer are shown in Table 1.

Synthesis Example 6

Forty parts by mass of a commercial PVA resin (manufactured by JAPAN VAM & POVAL CO., LTD., JL-05E, saponification value: 80.2 mol %, viscosity of 4% by mass aqueous solution: 5.1 mPa·s) and 60 parts by mass of a commercial PVA resin (manufactured by JAPAN VAM & POVAL CO., LTD., JT-05, saponification value: 94.0 mol %, viscosity of 4% by mass aqueous solution: 5.6 mPa·s) were placed into a polyethylene bag. The bag was shaken about 100 times so that the PVA powders were mixed into a homogeneous mixture. Thus, a PVA-based polymer having a broad saponification value distribution was prepared.

The measured physical properties of the obtained PVA-based polymer are shown in Table 1.

Synthesis Example 7

Ninety parts by mass of a commercial PVA resin (manufactured by JAPAN VAM & POVAL CO., LTD., JP-05, saponification value: 87.5 mol %, viscosity of 4% by mass aqueous solution: 5.3 mPa·s) and 10 parts by mass of a commercial PVA resin (manufactured by JAPAN VAM & POVAL CO., LTD., JT-05, saponification value: 94.0 mol %, viscosity of 4% by mass aqueous solution: 5.6 mPa·s) were placed into a polyethylene bag. The bag was shaken about 100 times so that the PVA powders were mixed into a homogeneous mixture. Thus, a PVA-based polymer having a broad saponification value distribution was prepared.

The measured physical properties of the obtained PVA-based polymer are shown in Table 1.

Synthesis Example 8

Sixty parts by mass of a commercial PVA resin (manufactured by JAPAN VAM & POVAL CO., LTD., JL-05E, saponification value: 80.2 mol %, viscosity of 4% by mass aqueous solution: 5.1 mPa·s) and 40 parts by mass of a commercial PVA resin (manufactured by JAPAN VAM & POVAL CO., LTD., JT-05, saponification value: 94.0 mol %, viscosity of 4% by mass aqueous solution: 5.6 mPa·s) were placed into a polyethylene bag. The bag was shaken about 100 times so that the PVA powders were mixed into a homogeneous mixture. Thus, a PVA-based polymer having a broad saponification value distribution was prepared.

The measured physical properties of the obtained PVA-based polymer are shown in Table 1.

Synthesis Example 9

A PVA-based polymer was obtained in the same manner as described in Comparative Synthesis Example 1 except that a commercial polyvinyl acetate resin (manufactured by JAPAN VAM & POVAL CO., LTD., JMR-10LL, polymerization degree: 250) was used as the polyvinyl acetate resin.

The measured physical properties of the obtained PVA-based polymer are shown in Table 1.

Synthesis Example 10

A PVA-based polymer was obtained in the same manner as described in Comparative Synthesis Example 1 except that a polyvinyl acetate resin having a polymerization degree of 800 was used as the polyvinyl acetate resin.

The measured physical properties of the obtained PVA-based polymer are shown in Table 1.

Synthesis Example 11

Ninety-three parts by mass of a commercial PVA resin (manufactured by JAPAN VAM & POVAL CO., LTD., JP-05, saponification value: 87.5 mol %, viscosity of 4% by mass aqueous solution: 5.3 mPa·s) and 7 parts by mass of a commercial PVA resin (manufactured by JAPAN VAM & POVAL CO., LTD., JT-05, saponification value: 94.0 mol %, viscosity of 4% by mass aqueous solution: 5.6 mPa·s) were placed into a polyethylene bag. The bag was shaken about 100 times so that the PVA powders were mixed into a homogeneous mixture. Thus, a PVA-based polymer having a broad saponification value distribution was prepared.

The measured physical properties of the obtained PVA-based polymer are shown in Table 1.

The results are summarized in Table 1 below. In Table 1, "P" in parentheses means passing requirement (A), and "F" means failing requirement (A).

In Table 1, the physical properties of the commercial PVA-based polymer (manufactured by JAPAN VAM &

POVAL CO., LTD., JP-05) used in Comparative Example 3 described later are also shown.

TABLE 1

| PVA-based polymer | Average saponification value (mol %) | Viscosity of 4% by mass aqueous solution (mPa · s) | Value of formula (3) |
|---|---|---|---|
| Synthesis Example 1 | 88.2 | 5.2 | 43[P] |
| Synthesis Example 2 | 88.3 | 5.2 | 51[P] |
| Synthesis Example 3 | 88.3 | 5.3 | 40[P] |
| Synthesis Example 4 | 88.2 | 5.2 | 60[P] |
| Synthesis Example 5 | 88.4 | 5.3 | 70[P] |
| Synthesis Example 6 | 88.5 | 5.4 | 49[P] |
| Synthesis Example 7 | 88.2 | 5.5 | 30[P] |
| Synthesis Example 8 | 85.7 | 5.1 | 49[P] |
| Synthesis Example 9 | 88.3 | 3.0 | 45[P] |
| Synthesis Example 10 | 88.2 | 8.1 | 32[P] |
| Synthesis Example 11 | 88.1 | 5.4 | 24[P] |
| Comparative Synthesis Example 1 | 88.3 | 5.3 | 12[F] |
| Comparative Synthesis Example 2 | 88.3 | 5.2 | 18[F] |
| JP-05 | 88.2 | 5.3 | 13[F] |

Example 1

Ten parts by mass of the PVA-based polymer obtained in Synthesis Example 1 was added to 240 parts by mass of purified water, and the mixture was stirred with heating to 80° C. for 1 hour to prepare a binder solution (PVA-based polymer concentration: 4% by mass). This binder solution was sprayed onto a powder mix of 400 g of lactose and 100 g of acetaminophen (average particle diameter: 40 μm) in a fluid bed granulator to produce granules [average particle diameter: 200 μm, 0.02 part by mass of the PVA-based polymer per part by mass of the powder (2.0% by mass of the PVA-based polymer per granule)].

After granulation, 475.0 g of the obtained granules and 25.0 g of a low-substituted hydroxypropyl cellulose were placed into a polyethylene bag, and the bag was shaken 100 times. To the bag, 2.5 g of magnesium stearate was added, and the bag was further shaken 30 times to give a powder for tableting (average particle diameter: 180 μm).

The powder for tableting was subjected to tableting to produce tablets. The obtained tablet was measured in terms of tablet hardness and disintegration time.

The disintegration time considerably varies with the value of tablet hardness. For this reason, comparison has to be made under the same tablet hardness conditions. To this end, tablets were produced by granulation and tableting using binder solutions at different concentrations (different proportions of the binder) (0 part by mass, 0.01 part by mass, and 0.03 part by mass of the PVA-based polymer relative to 1 part by mass of a granule), and based on the tablet hardness results, the disintegration time was calculated (estimated) at a tablet hardness of 90 N.

The results are shown in Table 2.

Examples 2 to 11

Tablets were produced in the same manner as described in Example 1 except that granulation was performed using the PVA-based polymers obtained in Synthesis Examples 2 to 11 instead of the PVA-based polymer obtained in Synthesis Example 1. The obtained tablets were evaluated in terms of tablet hardness and disintegration time in the same manner as described in Example 1. The results are shown in Table 2.

Comparative Example 1

Tablets were produced in the same manner as described in Example 1 except that granulation was performed using the PVA-based polymer obtained in Comparative Synthesis Example 1 instead of the PVA-based polymer obtained in Synthesis Example 1. The obtained tablets were evaluated in terms of tablet hardness and disintegration time in the same manner as described in Example 1. The results are shown in Table 2.

Comparative Example 2

Tablets were produced in the same manner as described in Example 1 except that granulation was performed using the PVA-based polymer obtained in Comparative Synthesis Example 2 instead of the PVA-based polymer obtained in Synthesis Example 1. The obtained tablets were evaluated in terms of tablet hardness and disintegration time in the same manner as described in Example 1. The results are shown in Table 2.

Comparative Example 3

Tablets were produced in the same manner as described in Example 1 except that granulation was performed using the commercial partially-saponified PVA (manufactured by JAPAN VAM & POVAL CO., LTD., JP-05) instead of the PVA-based polymer obtained in Synthesis Example 1. The obtained tablets were evaluated in terms of tablet hardness and disintegration time in the same manner as described in Example 1. The results are shown in Table 2.

TABLE 2

| | PVA-based polymer | Tablet hardness (N) | Disintegration time (min) |
|---|---|---|---|
| Example 1 | Synthesis Example 1 | 92 | 100 |
| Example 2 | Synthesis Example 2 | 93 | 99 |
| Example 3 | Synthesis Example 3 | 92 | 105 |
| Example 4 | Synthesis Example 4 | 95 | 99 |
| Example 5 | Synthesis Example 5 | 93 | 98 |
| Example 6 | Synthesis Example 6 | 90 | 125 |
| Example 7 | Synthesis Example 7 | 87 | 170 |
| Example 8 | Synthesis Example 8 | 92 | 98 |
| Example 9 | Synthesis Example 9 | 90 | 95 |

TABLE 2-continued

|  | PVA-based polymer | Tablet hardness (N) | Disintegration time (min) |
|---|---|---|---|
| Example 10 | Synthesis Example 10 | 93 | 195 |
| Example 11 | Synthesis Example 11 | 85 | 198 |
| Comparative Example 1 | Comparative Synthesis Example 1 | 83 | 215 |
| Comparative Example 2 | Comparative Synthesis Example 2 | 81 | 200 |
| Comparative Example 3 | JP-05 | 82 | 210 |

As is clear from the results in Table 2, the tablets containing, as a binder, the PVA-based polymer which meets requirement (A) showed a shorter disintegration time as compared with the tablets containing, as a binder, the PVA-based polymer which fails requirement (A), when compared under the same hardness conditions. In addition, the tablets containing, as a binder, the PVA-based polymer which meets requirement (A) showed a larger hardness (that is, higher moldability) as compared with the tablets containing, as a binder, the PVA-based polymer which fails requirement (A).

Surprisingly, the binder which meets requirement (A) was found to achieve a good balance between hardness and disintegrability, which originally have a trade-off relationship.

INDUSTRIAL APPLICABILITY

The present invention provides a novel binder. The binder is useful for various applications including the production of granulated materials from powder particles.

The invention claimed is:

1. A binder comprising a polyvinyl alcohol-based polymer, wherein the polyvinyl alcohol-based polymer has an average saponification value of 85.0 mol % to 89.0 mol % as measured according to JIS K6726,
   wherein the polyvinyl alcohol-based polymer is a saponified product of a polymer composed of a vinyl acetate as a polymerization component, and
   wherein the polyvinyl alcohol-based polymer meets the following requirement (A): based on data obtained by measurement of the polyvinyl alcohol-based polymer by liquid chromatography, a value represented by Formula (3) shown below is 22 or more,
   wherein the measurement is performed with a liquid chromatography system equipped with a charged aerosol detector and a column comprising the following: carbon load: 8%, maximum pressure: 4500 psi, particle size: 3 μm, pore size: 300 Å, stationary phase: C18, surface area: 100 m²/g, length: 150 mm, diameter: 4.6 mm, pH: 2.5 to 7.5, material: glass lined tubing, and under the measurement conditions described below,
   wherein the data represent a baseline-normalized intensity over a retention time of 5.0 to 12.0 minutes at a sampling interval of 500 ms, and
   wherein the value represented by Formula (3) is calculated from Formulae (1) and (2) shown below, wherein the intensity at a retention time $T_i$ [min] is represented by $P_i$ [pA];

Measurement Conditions:
   Concentration of an aqueous polyvinyl alcohol-based polymer solution: 0.1% by mass
   Injection volume of the aqueous polyvinyl alcohol-based polymer solution: 2 μL
   Column temperature: 50° C.
   Flow rate: 1.0 mL/min
   Eluent: a mixed solvent of water and methanol
   Eluent gradient conditions: the ratio of water and methanol in the eluent changes from 95:5 to 15:85 at a constant rate over a run time from minutes 0 to 10; and the ratio of water and methanol in the eluent is constant at 15:85 over a run time from minutes 10 to 15;

Formulae:

$$T_n = \Sigma(T_i \times P_i)/\Sigma(P_i) \qquad \text{Formula (1)}$$

$$T_w = (T_i^2 \times P_i)/\Sigma(T_i \times P_i) \qquad \text{Formula (2)}$$

$$\{(T_w/T_n) - 1\} \times 1000 \qquad \text{Formula (3)}.$$

2. The binder according to claim 1, wherein the value represented by Formula (3) specified in requirement (A) is 30 or more.

3. The binder according to claim 1, wherein the value represented by Formula (3) specified in requirement (A) is 33 or more.

4. The binder according to claim 1, wherein a 4% by mass aqueous solution of the polyvinyl alcohol-based polymer has a viscosity of 2.0 to 10.0 mPa·s as measured according to JIS K6726.

5. The binder according to claim 1, wherein the binder is used for granulation.

6. The binder according to claim 1, wherein the binder is used for granulation from powder particles having an average particle diameter of 100 μm or less.

7. The binder according to claim 1, wherein the binder is used for production of a granulated material having an average particle diameter of 300 μm or less.

8. A method for producing a granulated material by granulation using the binder according to claim 1.

9. The method according to claim 8, wherein the method comprises a step of bringing an aqueous and/or water-based solution containing the binder into contact with powder particles.

10. A granulated material comprising the binder according to claim 1 as a binder.

11. The granulated material according to claim 10, wherein the binder is present in an amount of 0.005 to 0.1 part by mass relative to 1 part by mass of powder particles.

12. A tablet comprising the granulated material according to claim 10.

13. A coated tablet comprising the tablet according to claim 12 and a polyvinyl alcohol-based polymer coating a surface of the tablet.

14. The binder according to claim 1, wherein the binder is not used in a composition comprising at least one compound selected from the group consisting of levodopa, carbidopa and irbesartan.

15. The method according to claim 8, wherein the granulated material does not comprise at least one compound selected from the group consisting of levodopa, carbidopa and irbesartan.

16. The granulated material according to claim 10, wherein the granulated material does not comprise at least one compound selected from the group consisting of levodopa, carbidopa and irbesartan.

* * * * *